US008222450B2

(12) United States Patent
Besson

(10) Patent No.: US 8,222,450 B2
(45) Date of Patent: Jul. 17, 2012

(54) PREPARATION OF SULFONIC ACID ANHYDRIDES

(75) Inventor: Bernard Besson, Les Echets (FR)

(73) Assignee: Aubervilliers (FR)

( * ) Notice: Subject to any disclaimer, the term of this patent is extended or adjusted under 35 U.S.C. 154(b) by 350 days.

(21) Appl. No.: 12/375,073

(22) PCT Filed: Jul. 25, 2007

(86) PCT No.: PCT/FR2007/001276
§ 371 (c)(1),
(2), (4) Date: Oct. 9, 2009

(87) PCT Pub. No.: WO2008/012433
PCT Pub. Date: Jan. 31, 2008

(65) Prior Publication Data
US 2010/0076221 A1    Mar. 25, 2010

(30) Foreign Application Priority Data
Jul. 27, 2006 (FR) ..................... 06 06881

(51) Int. Cl.
*C07C 303/00* (2006.01)
(52) U.S. Cl. ...................................... 562/872
(58) Field of Classification Search ............ None
See application file for complete search history.

(56) References Cited

U.S. PATENT DOCUMENTS 5,808,149 A    9/1998 Nakamura et al.
6,469,206 B2 * 10/2002 Hembre et al. ............ 562/872

FOREIGN PATENT DOCUMENTS
WO    WO 01/66516 A1    9/2001

OTHER PUBLICATIONS

Chase et al.,"Ring-chain tautomerism in the acid hallides of the half-esters of dibasic acids," J.Chem.Soc., (1952) 553-572.*
M. Karger et al. "Mixed Sulfonic-Carboxylic Anhydrides. I. Synthesis and thermal stability. New syntheses of sulfonic anhydrides," J.Org.Chem., (1971) 36:528-531.*
Jones, P. "Ring-chain tautomerism" Chem. Rev., (1963) 461-487.*
Bhatt et al., "Aspects of Tautomerism: Part X+ -Neighbouring Group Effects on the Structure & Reactivity Patterns of Acid Chlorides", Indian Journal of Chemistry, 1980, pp. 473-486, vol. 19B.

* cited by examiner

*Primary Examiner* — Porfirio Nazario Gonzalez
*Assistant Examiner* — James Meadows
(74) *Attorney, Agent, or Firm* — SNR Denton US LLP

(57) ABSTRACT

Sulfonic acid anhydrides, and more particularly triflic anhydride, are prepared by reacting a sulfonic acid or a mixture of two sulfonic acids with a reactant exhibiting acid pseudohalide tautomerism and containing at least one carbon atom which is involved in the tautomerism bearing two halogen atom substituents.

25 Claims, No Drawings

PREPARATION OF SULFONIC ACID ANHYDRIDES

CROSS-REFERENCE TO PRIORITY/PCT APPLICATIONS

This application claims priority under 35 U.S.C. §119 of FR 0606881, filed Jul. 27, 2006, and is a continuation/national phase of PCT/FR 2007/001276, filed Jul. 25, 2007 and designating the United States (published in the French language on Jan. 31, 2008, as WO 2008/012433 A2; the title and abstract were also published in English), each hereby expressly incorporated by reference in its entirety and each assigned to the assignee hereof.

The present invention relates to a process for preparing a sulfonic acid anhydride.

It concerns the preparation of a symmetrical or mixed anhydride.

More particularly, it pertains to the preparation of an anhydride derived from a sulfonic superacid.

More specifically, the invention pertains to the preparation of trifluoromethanesulfonic anhydride, also known as "triflic anhydride".

Sulfonic superacids, i.e. those with a Hammett constant of at least 12, advantageously 13, are being used more and more frequently as intermediates in synthesis, in particular to form particularly reactive leaving groups.

Such sulfonic superacids are generally sulfonic acids wherein the sulfur carries a fluorinated function, in general a group carrying a difluoromethylene motif linking the sulfur of the sulfonic function to the remainder of the molecule of the acid.

In order to graft such sulfonyl groups, it is possible to use sulfonyl halides. However, such sulfonyl halides can be difficult to use. The fluoride group of the sulfonyl has a relatively low reactivity. The chloride and the bromide have oxidizing properties, i.e. are respectively chlorinating or brominating, which renders them difficult to use for a large number of applications.

For this reason, the anhydride, either symmetrical or mixed, remains a means for grafting sulfonyl groups without such disadvantages.

However, synthesizing such sulfonic anhydrides is still very difficult, and the only really effective technique which has been discovered up to now resides in bringing the sulfonic acids envisaged in the present invention into contact with phosphoric anhydride ($P_2O_5$). Reference may in particular be made to U.S. Pat. Nos. 5,004,829 and 5,808,149.

The dehydration reaction between two molecules of sulfonic acid runs well, but the quantity of phosphoric acid and the difficulty of selecting a suitable solvent render the operation particularly difficult and expensive to carry out, especially as regards problems with stirring, which has to be carried out in a medium which is particularly aggressive.

The aim of the present invention is to furnish a process which overcomes the cited disadvantages.

A process has now been discovered, and this constitutes the subject matter of the present invention, for preparing a sulfonic acid anhydride, characterized in that it comprises reacting a sulfonic acid or a mixture of two sulfonic acids with a reagent exhibiting acid pseudohalide tautomerism wherein at least one carbon atom engaged in the tautomerism carries two halogen atoms.

In the present text, the term "halogen" means fluorine, chlorine or bromine, more particularly the chlorine atom.

The term "halophore group" means a carbon atom which carries one, two or three halogen atoms.

The term "gem-dihalogenated" means a group having two halogen atoms on the same carbon atom.

In accordance with the process of the invention, it is possible to form a sulfonic anhydride function from sulfonic groups by eliminating a water molecule by dint of the presence of a molecule exhibiting acid pseudohalide tautomerism.

Such molecules have been widely described in the literature, in particular by M Vivekananda Bhatt et al. (Indian Journal of Chemistry, 19B, June 1980, pp 437-486).

Thus, the process of the invention involves a reagent the characteristic of which is to have, under the reaction conditions, a tautomeric form of the pseudohalide type, i.e. a cyclic structure.

For the same chemical formula, an organic compound may have one or more electronic structures which are in equilibrium.

Tautomers are organic compounds which are interchangeable by tautomerization.

Acid pseudohalide tautomerism starting from an acid halide is the creation of a cyclic compound comprising an oxygen bridge between a gem-dihalogenated group and a carbonyl (or sulfonyl) group or a gem-dihalogenated group and a halophore group which is a mono-halogenated carbon atom or a gem-dihalogenated group.

The reagent of the invention, which for simplicity is denoted the "reagent" in the remainder of the text, must have a tautomeric form of the pseudohalide type, but also the carbon atom which is engaged in the tautomerism carries two halogen atoms.

In accordance with the process of the invention, the reagent must have a cyclic type tautomeric form which comprises the following motif in equilibrium with its tautomeric form:

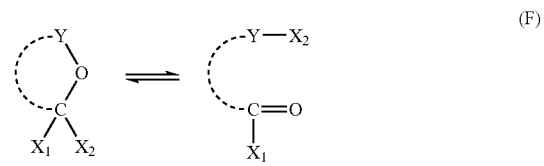

(F)

in said formula (F):
Y represents one of the following groups:
  CO;
  $SO_2$;
  $CX_1', X_2'$;
$X_1$, $X_2$ represent a halogen atom; preferably, $X_1$, $X_2$ both represent a chlorine atom;
$X_1'$, $X_2'$ represent a hydrogen atom or a halogen atom, and at most one of $X_1'$, $X_2'$ represents a hydrogen atom;
the semi-circle symbolized by the dashes represents a divalent group comprising 2 to 4 carbon atoms:
  which is a linear hydrocarbon chain comprising at least one double bond;
  or which forms part of one or two unsaturated or aromatic cycles.

The term "unsaturated cycle" as used in the present text means a hydrocarbon cycle containing 5 or 6 carbon atoms, preferably 6 atoms, comprising one or two double bonds.

The term "aromatic cycle" as used in the present text means an aromatic hydrocarbon cycle or bi-cycle containing 6 to 12 carbon atoms, preferably a benzene ring.

In formula (F), the semi-circle symbolizes atoms which are present in the heterocycle allowing tautomerism to occur.

Hence, the invention does not exclude other aliphatic or aromatic structures provided that the heterocyclic structure can produce the tautomerism.

Similarly, the invention does not exclude the presence of substituents on the vacant sites of the double bonds or on the cycle provided that they do not react. In particular, it is possible to cite $C_1$-$C_4$ alkoxy or alkyl groups or halogen atoms, preferably chlorine or bromine.

Clearly, the functions present in the motif with formula (F) must be topologically close so as to be joined by said oxygen bridge thereby forming a heterocycle of at most 7 atoms, preferably 5 or 6 atoms.

Advantageously, in an aliphatic hydrocarbon chain, the halophore group $CX_1X_2$ is in the γ or δ position with respect to Y, preferably in the γ position.

In formula (F), the semi-circle represented by dashes preferably represents an aliphatic chain comprising one or two double bonds, preferably an ethylene linkage.

When one or two double bonds are included in one or two cycles, in formula (F) the semi-circle represented by the dashes preferably represents an aromatic group such as a 1,2-phenylene group or a 1,2-naphthyldiyl group or a 1,8-naphthyldiyl group.

As mentioned above, the vacant bonds of the double bond or the free positions of the reagents comprising a cycle may carry a substituent, for example halogen atoms.

Thus, a first class of preferred reagents has the following formulae in equilibrium with their tautomeric forms:

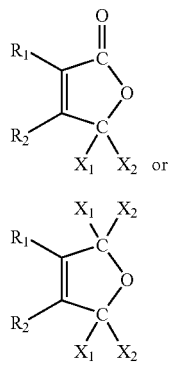

in said formulae:
$R_1$, $R_2$ represent a hydrogen atom, a linear or branched alkyl group containing 1 to 4 carbon atoms, or a halogen atom;
or $R_1$ and $R_2$ are linked to form a 1,2-phenylene group or a 1,2-naphthyldiyl group;
$X_1$, $X_2$ represent a halogen atom; preferably, $X_1$, $X_2$ both represent a chlorine atom.

Thus, preferred reagents used in the process of the invention have formula (Ia) or (Ib) (and their tautomeric forms) in which $R_1$ and $R_2$ represent a hydrogen atom or a methyl group or $R_1$ and $R_2$ are linked to form one of the following groups:

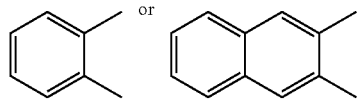

As mentioned above, the invention includes the case where the aromatic cycles carry substituents. Any substituent may be present provided that it does not hinder production of the desired product.

Examples were given above.

Examples of reagents present during the reaction are given below:

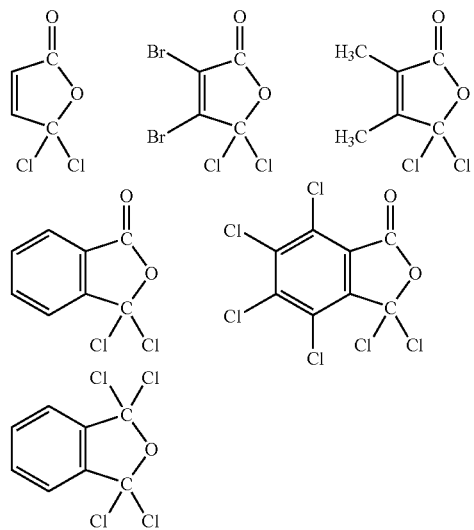

The reagent which is preferred comprises the motif represented by the following formula in equilibrium with its tautomeric form:

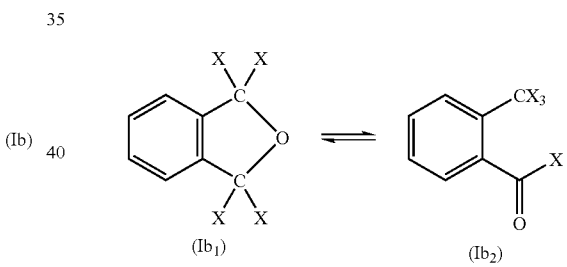

in said formulae, X is a halogen atom, preferably a chlorine atom.

Another class of preferred reagents consists of those in which the functional groups Y and $CX_1X_2$ are carried by a carbon atom belonging to two different benzene rings but which are ortho-condensed.

An example of this type of reagent is given by that which has the following formula (Ic):

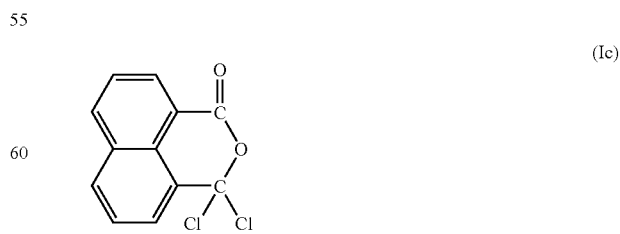

The various reagents are known products which are commercially available or described in the literature, especially by M Vivekananda Bhatt et al. (loc cit).

The sulfonic acid may be represented by the following formula:

$$R_f\text{—}SO_3H \quad (II)$$

in said formula:
  $R_f$ represents a hydrocarbon group containing 1 to 20 carbon atoms which may or may not comprise at least one halogen atom, preferably a fluorine atom,
In formula (II), $R_f$ preferably represents a hydrocarbon group containing 1 to 20 carbon atoms; more particularly:
  a linear or branched alkyl group containing 1 to 12 carbon atoms;
  a linear or branched alkenyl or alkynyl group containing 2 to 12 carbon atoms;
  a cycloalkyl or cycloalkenyl group containing 3 to 8 carbon atoms;
  an aryl group containing 6 to 20 carbon atoms, preferably a phenyl group or a naphthyl group;
  an arylalkyl group containing 7 to 20 carbon atoms, preferably a benzyl group.

The various groups cited above, namely alkyl, alkenyl, alkynyl, cycloalkyl, aryl or arylalkyl may be substituted with any substituent provided that it does not hinder the reaction. More particular examples of substituents which may be mentioned, inter alia, are halogen atoms, preferably fluorine, chlorine or bromine.

More precisely, in formula (II), $R_f$ represents a hydrocarbon group containing 1 to 20 carbon atoms, and more particularly:
  a $C_1$ to $C_{10}$ alkyl group, preferably $C_1$ to $C_4$, and more preferably a methyl or ethyl group;
  a $C_1$ to $C_{10}$ alkyl group, preferably $C_1$ to $C_4$, mono-, poly- or per-halogenated, containing 1 to 23 halogen atoms, preferably a $CF_3$ group;
  a cycloalkyl group containing 3 to 8 carbon atoms, preferably a cyclohexyl group;
  a cycloalkyl group, optionally mono-, poly- or per-halogenated, containing 3 to 8 carbon atoms;
  a phenyl group;
  a mono-, poly- or per-halogenated phenyl group;
  a phenyl group substituted with at least one $C_1$ to $C_{10}$ alkyl group, preferably $C_1$ to $C_4$, optionally mono-, poly- or per-halogenated or a nitro or nitrile group;
  an aryl group, optionally mono-, poly- or per-halogenated, containing 6 to 12 carbon atoms.

More preferably, $R_f$ represents a methyl, a phenyl, or a tolyl group, a $CF_3$ group, a $C_4F_9$ group or a phenyl group substituted with one or more halogen atoms, preferably fluorine, or with one or more mono-, poly- or per-fluorinated $C_1$-$C_2$ alkyl groups.

Examples of sulfonic acids which may in particular be mentioned are halogenosulfonic acids, preferably fluorosulfonic acid, chlorosulfonic acid, trifluoromethanesulfonic acid, perfluoroethanesulfonic acid, perfluorobutanesulfonic acid, perfluorooctanesulfonic acid; aliphatic sulfonic acids, preferably methanesulfonic acid, ethanesulfonic acid; aromatic sulfonic acids, preferably benzenesulfonic acid, toluenesulfonic acids, and naphthalenesulfonic acids.

Preferred acids from those above are trifluoromethanesulfonic acid, para-toluenesulfonic acid, methanesulfonic acid and benzenesulfonic acid.

In accordance with the process of the invention, the reagent defined in accordance with the invention is reacted with the sulfonic acid.

The quantity of reagent employed is generally a function of the number of gem-dihalogenated groups present in formula (I) and engaged in the tautomerism reaction.

Thus, in the case of a reagent comprising a gem-dihalogenated group as in formula (Ia) or (Ic), the quantity thereof which is employed is such that the ratio between the number of moles of reagent comprising a gem-dihalogenated group, preferably with formula (Ia) or (Ic), and the number of moles of sulfonic acid is advantageously selected to be in the range 0.5 to 1, preferably in the range 0.5 to 0.7.

When the reagent comprises two gem-dihalogenated groups, the quantity thereof employed is such that the ratio between the number of moles of reagent comprising two gem-dihalogenated groups, preferably with formula (Ib), and the number of moles of sulfonic acid is advantageously selected to be in the range 0.25 to 0.5, preferably in the range 0.25 to 0.35.

The reaction may be carried out in the presence of solvents which are inert towards the two reagents and the products of the reaction.

Examples of solvents which are capable of being used which may in particular be cited are aliphatic hydrocarbons, cycloaliphatic hydrocarbons or aromatic hydrocarbons, preferably hexane, cyclohexane, methylcyclohexane, heptane, dodecane, benzene, toluene, xylenes, ethylbenzene, diethylbenzenes, trimethylbenzenes, cumene, pseudocumene, and oil cuts constituted by a mixture of alkylbenzenes, in particular Solvesso® type cuts.

However, the process of the invention is preferably carried out in the absence of organic solvents.

The reaction is carried out at normal pressure, but this is not critical. The reaction is advantageously carried out at a temperature in the range 80° C. to 180° C., preferably in the range 100° C. to 150° C.

The optimized temperature is in the range 110° C. to 140° C.

The process is simple to carry out. The reagent and the sulfonic acid are mixed in any order, generally at ambient temperature (usually in the range 15° C. to 25° C.), then the temperature is increased until the halohydric acid is given off, preferably the hydrochloric acid which is formed during the reaction.

A preferred mode consists of heating the reagent to the selected reaction temperature, then progressively adding the sulfonic acid, preferably using a dropping funnel.

The process of the invention may be carried out continuously, for example in a distillation apparatus with a short residence time (such as a LUWA® apparatus).

It may also be carried out discontinuously in a conventional reactor provided with stirring means and heating means surmounted by a distillation column.

The reaction temperature may be controlled, either using a heat exchanger or by circulating a liquid coolant in a jacket with which it is provided.

Liquid coolants which are suitable for use in the invention which may in particular be mentioned are water or an organic solvent such as one selected from heavy carboxylic acid esters (for example octyl phthalate), aromatic ethers such as biphenyl oxide and/or benzyl oxide, biphenyl, terphenyls, other polyphenyls which may be partially hydrogenated, paraffin oils and/or naphthene oils, oil distillation residues, etc.

The gaseous stream collected at the column head comprising the halohydric acid is condensed by passage through one or more heat exchangers cooled with water, glycolated water or any other liquid coolant which is compatible with the selected cooling temperature.

In accordance with the process of the invention, a symmetrical or mixed sulfonic anhydride is obtained which may be symbolized by formula (III):

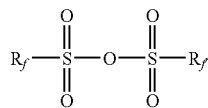

(III)

in which formula:
$R_f'$ has the meaning given for $R_f$;
$R_f$ is identical to $R_f'$ in the case of symmetrical anhydrides; and $R_f'$ is different from $R_f'$ in the case of mixed anhydrides.

Recovery of the sulfonic anhydride formed from the reaction medium falls within the field of competence of the skilled person.

Several recovery modes may be envisaged which depend on the boiling point of the sulfonic anhydride formed.

In the case of triflic anhydride, this latter constitutes a gaseous stream with the halohydric acid which is recovered by condensation in an exchanger. The halohydric acid is sent to a sodium hydroxide extraction column.

If the temperature at which the sulfonic anhydride formed boils is higher than the reaction temperature, the sulfonic anhydride remains in the reaction medium in the distillation residue while the halohydric acid is recovered from the distillation head.

If the sulfonic anhydride formed remains in the distillation residue, it may be recovered subsequently using any suitable means, in particular by distillation, usually by distillation under reduced pressure.

Non-limiting examples will be given below by way of illustration.

In the examples, the abbreviations used have the following meanings:
RO=benzoyl o-trichloromethyl chloride;
TA=trifluoromethanesulfonic acid=triflic acid;
TAA=trifluoromethanesulfonic anhydride=triflic anhydride;
PA=phthalic anhydride.

The yield (RR) corresponds to the ratio between the number of moles of product formed and the number of moles of substrate engaged.

EXAMPLES

Example 1

Preparation of Triflic Anhydride

A 250 ml reactor was used, heated with a double jacket and provided with a central mechanical stirrer, a dropping funnel and a swan neck adapter supplying a collector cooled to 15° C. and venting to the atmosphere via a) a dry ice trap b) a wash bottle containing a solution of sodium hydroxide.

73 g of RO which constituted the "seed" of the reaction mixture was loaded therein; the benzoyl trichloromethyl chloride employed was in equilibrium with its pseudochloride tautomeric form in a molar ratio of 20/80.

This seed was heated to 120° C.

157 g of triflic acid was progressively added using the dropping funnel over 3 hours, holding the temperature of the reaction mass to between 115° C. and 135° C.

Right from the start of addition, HCl release was observed and after approximately 15 min, crude TAA had condensed.

The HCl stream was turned into organic vapor by condensing it in the dry ice trap.

After addition was complete, the residue was consumed by heating for 5 min at 140° C. The reaction was halted when no more distillation occurred.

Crude TAA (condensate and trapped matter), the reaction residue and the washing solution were recovered.

They were analyzed using suitable methods (fluorine NMR, ion chromatography and potentiometry).

The following results were obtained:
RR of triflic anhydride: 91.4 mole %;
RR of trifluoromethylsulfonyl chloride: 0.34 mole %;
RR of trifluoromethyl triflate: 0.07 mole %.

Examples 2 and 3

Comparative Tests A to O

A series of qualitative type tests was carried out to demonstrate the influence of the nature of the reagent employed.

Before detailing the examples and tests, a description of the apparatus used and the operating protocol followed will be provided.

Apparatus Used

The apparatus used was a BUCHI® temperature gradient oven (Glass oven B 580).

It was in the form of a tubular glass oven into which a single-necked reactor flask, to which two receptor flasks were connected, was introduced.

The assembly was cohesive and could be rotated by a motor.

The light products from the reaction were trapped at the outlet by dry ice in two receptor flasks.

Any gas emission was monitored visually with a bubble counter.

Operating Protocol

The reagents were weighed in a hood in the reactor flask (max weight 10 g).

The molar ratio between the sulfonic acid and the reagent is shown in the tables below.

The two receptor flasks were added in-line and the assembly was held together with metal clips.

The reactor flask and the first receptor flask were inserted in the temperature gradient oven.

The second receptor flask was placed outside and cooled using dry ice.

The flask assembly was rotated and the oven temperature was gradually heated in 10 degree stages to a temperature slightly below the distillation temperature of the most volatile compound.

The temperature was held for thirty minutes and gas formation and distillation of trappable compounds was monitored visually.

After this holding stage, the temperature was dropped back to ambient temperature and the distillate recovered in the receptor flask outside the oven was analyzed by NMR or ion chromatography.

Tests A to K

In these tests, the sulfonic acid used was triflic acid and the reagents used were mono- and bi-functional acid chlorides.

The results are shown in Table (I).

TABLE (I)

| Test ref | Nature of reagent | Boiling point | Sulfonic acid/reagent ratio | Distillation |
|---|---|---|---|---|
| A | Benzoyl chloride | 198° C. | 2 | No |
| B | Pivaloyl chloride | 105° C. | 1 | No |
| C | Propionyl chloride | 77-79° C. | 1 | No |
| D | Acetyl chloride | 52° C. | 1 | No |
| E | Trichloroacetyl chloride | 115° C. | 1 | No |
| F | Adipoyl chloride | 106° C. 2 mm Hg | 1 | No |
| G | Succinyl chloride | 190° C. | 1 | No |
| H | Malonyl chloride | 54° C. 19 mm Hg | 1 | No |
| I | Oxalyl chloride | 62-63° C. | 1 | No |
| J | Terephthaloyl chloride | 266° C. | 2 | No |
| K | Isophthaloyl chloride | 276° C. | 2 | No |

No distillate was observed. Thus, no triflic anhydride had formed.

Tests L to N

In these tests, the sulfonic acid used was triflic acid and the reagent used was a compound with a trichloromethyl function.

The results are shown in Table (II).

TABLE (II)

| Test ref | Nature of reagent | Boiling point | Sulfonic acid/reagent ratio | Distillation |
|---|---|---|---|---|
| L | 1,4-bis-trichloromethyl benzene | 312° C. | 2 | No |
| M | Trichlorotoluene | 219-223° C. | 2 | No |
| N | 4-chlorotrichloro-methyl benzene | 245° C. | 1 | No |

No distillate was observed. Thus, no triflic anhydride had formed.

Test O

In this test, the sulfonic acid used was triflic acid and the reagent used was a compound with a gem-dichlorinated carbon not involved in the acid pseudochloride tautomerism.

The results are shown in Table (III).

TABLE (III)

| Test ref | Nature of reagent | Sulfonic acid/reagent ratio | Distillation |
|---|---|---|---|
| O | 2.2-dichlorobenzodioxole | 1 | No |

No distillate was observed. Thus, no triflic anhydride had formed.

Example 2

In this example, the sulfonic acid used was triflic acid and the reagent used was a compound having at least one gem-dichlorinated carbon atom involved in acid pseudochloride tautomerism.

The results are shown in Table (IV).

TABLE (IV)

| Test ref | Nature of reagent | Boiling point | Sulfonic acid/reagent ratio | Distillation |
|---|---|---|---|---|
| 2 | 2-trichloromethyl-benzoyl chloride | >150° C. | 2 | yes |

The recovered distillate was analyzed by fluorine magnetic resonance spectroscopy. It was essentially constituted by triflic anhydride.

Example 3

In this example, the sulfonic acid employed was methanesulfonic acid and the reagent was that from Example 2.

The results are shown in Table (V).

TABLE (V)

| Test ref | Nature of reagent | Boiling point | Sulfonic acid/reagent ratio |
|---|---|---|---|
| 3 | 2-trichloromethylbenzoyl chloride | 167° C. 10 mmHg | 2 |

In this example, there was no distillate but a release of an acidic gas was observed and analysis of the residual white product in the reactor flask showed that it was partially constituted by methanesulfonic anhydride and by phthalic anhydride.

The invention claimed is:

1. A process for preparing a sulfonic acid anhydride, comprising reacting a sulfonic acid or a mixture of two sulfonic acids with a reagent exhibiting acid pseudohalide tautomerism and containing at least one carbon atom engaged in the tautomerism bearing two halogen atom substituents, wherein the sulfonic acid has the following formula:

$$R_f\text{---}SO_3H \qquad (II)$$

in which $R_f$ is a hydrocarbon radical having 1 to 20 carbon atoms which comprises at least one halogen atom.

2. The process as defined by claim 1, wherein the halogen is fluorine, chlorine or bromine.

3. The process as defined by claim 1, wherein said reagent has the following motif in equilibrium with its tautomeric form:

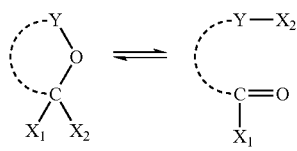

(F)

wherein in formula (F):
Y is one of the following groups:
   CO;
   SO$_2$;
   CX$_1$', X$_2$';
X$_1$, X$_2$ are each a halogen atom;
X$_1$', X$_2$' are each a hydrogen atom or a halogen atom, and at most one of X$_1$' and X$_2$' is a hydrogen atom;
the semi-circle symbolized by the dashes is a divalent radical containing 2 to 4 carbon atoms and which comprises a linear hydrocarbon chain containing at least one double bond, or which forms part of one or two unsaturated or aromatic cyclic ring members.

4. The process as defined by claim 3, wherein the semi-circle represented by the dashes in formula (F) is an aliphatic hydrocarbon chain comprising one or two double bonds or one or two double bonds are included in one or two cyclic ring members.

5. The process as defined by claim 4, wherein the semi-circle represented by the dashes in formula (F) is an ethylene linkage or a 1,2-phenylene group or a 1,2-naphthyldiylgroup or a 1,8-naphthyldiyl group.

6. The process as defined by claim 3, wherein the semi-circle represented by the dashes in formula (F) is an aliphatic hydrocarbon chain in which the halophore group CX$_1$X$_2$ is in the γ or δ position with respect to Y.

7. The process as defined by claim 1, wherein said reagent has the following formulae in equilibrium with the tautomeric forms thereof:

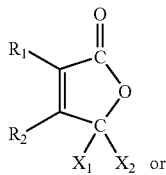

(Ia)

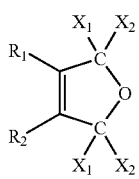

(Ib)

wherein said formulae:
R$_1$, R$_2$ are each a hydrogen atom, a linear or branched alkyl radical having 1 to 4 carbon atoms, or a halogen atom; or R$_1$ and R$_2$ are linked to form a 1,2-phenylene group or a 1,2-naphthyldiyl group, wherein the aromatic groups formed by the linkage of R$_1$ and R$_7$ optionally comprise one or more substituents that do not hinder production of the desired product; and
X$_1$, X$_2$ are each a halogen atom.

8. The process as defined by claim 7, wherein said reagent has formula (Ia) or (Ib) and the tautomeric forms thereof, in which R$_1$, R$_2$ are each a hydrogen atom or a methyl group or R$_1$ and R$_2$ are bonded to form one of the following groups:

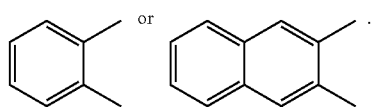 or 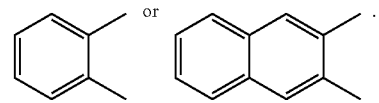.

9. The process as defined by claim 7, wherein said reagent has one of the following formulae:

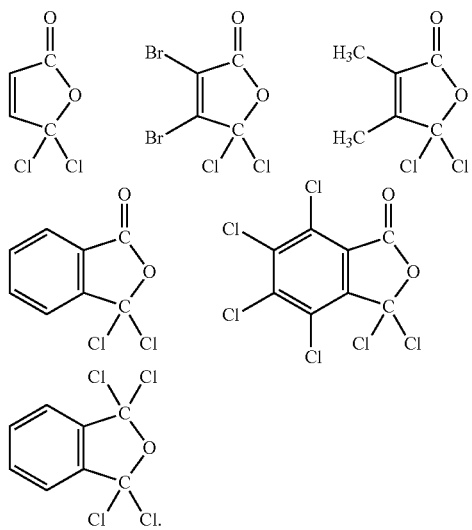

10. The process as defined by claim 3, wherein said reagent comprises the motif represented by the following formula in equilibrium with its tautomeric form:

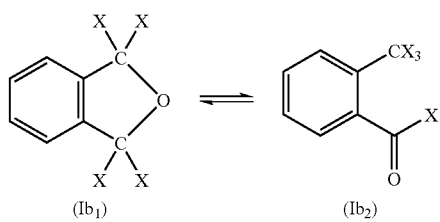

(Ib$_1$)         (Ib$_2$)

wherein said formulae, X is a halogen atom.

11. The process as defined by claim 3, wherein said reagent comprises functional groups Y and CX$_1$X$_2$ which are borne by a carbon atom belonging to two different benzene rings but which are ortho-condensed.

12. The process as defined by claim 11, wherein said reagent has the following formula:

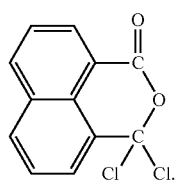

(Ic)

13. The process as defined by claim 1, wherein the hydrocarbon group $R_f$ is selected from the group consisting of:
- a linear or branched alkyl radical having 1 to 12 carbon atoms;
- a linear or branched alkenyl or alkynyl radical having 2 to 12 carbon atoms;
- a cycloalkyl or cycloalkenyl radical having 3 to 8 carbon atoms;
- an aryl radical having 6 to 20 carbon atoms, a phenyl radical or a naphthyl radical; and
- an arylalkyl radical having 7 to 20 carbon atoms, or a benzyl radical.

14. The process as defined by claim 1, wherein the sulfonic acid has formula (II) in which $R_f$ is:
- a $C_1$ to $C_{10}$ alkyl radical;
- a $C_1$ to $C_{10}$ alkyl radical, mono-, poly- or per-halogenated, having 1 to 23 halogen atoms
- a cycloalkyl radical having 3 to 8 carbon atoms;
- a cycloalkyl radical, mono-, poly- or per-halogenated, having 3 to 8 carbon atoms;
- a phenyl radical;
- a mono-, poly- or per-halogenated phenyl radical;
- a phenyl radical substituted with at least one $C_1$ to $C_{10}$ alkyl substituent, optionally mono-, poly- or per-halogenated or a nitro or nitrile group; or
- an aryl radical, optionally mono-, poly- or per-halogenated, having 6 to 12 carbon atoms.

15. The process as defined by claim 14, wherein the sulfonic acid has formula (II) in which $R_f$ is a methyl, a phenyl, or a tolyl group, a $CF_3$ group, a $C_4F_9$ group or a phenyl radical substituted with one or more halogen atoms, or with one or more mono-, poly- or per-fluorinated $C_1$-$C_2$ alkyl radicals.

16. The process as defined by claim 1, wherein the sulfonic acid is selected from the group consisting of halogenosulfonic acids, fluorosulfonic acid, chlorosulfonic acid, trifluoromethanesulfonic acid, perfluoroethanesulfonic acid, perfluorobutanesulfonic acid, perfluorooctanesulfonic acid; aliphatic sulfonic acids, methanesulfonic acid, ethanesulfonic acid; aromatic sulfonic acids, benzenesulfonic acid, toluenesulfonic acids, and naphthalenesulfonic acids.

17. The process as defined by claim 16, wherein the sulfonic acid is selected from the group consisting of trifluoromethanesulfonic acid, para-toluenesulfonic acid, methanesulfonic acid and benzenesulfonic acid.

18. The process as defined by claim 1, wherein the quantity of a reagent comprising a gem-dihalogenated group is such that the ratio of the number of moles of reagent comprising a gem-dihalogenated group to the number of moles of sulfonic acid ranges from 0.5 to 1.

19. The process as defined by claim 1, wherein the quantity of a reagent comprising two gem-dihalogenated groups is such that the ratio of the number of moles of reagent comprising two gem-dihalogenated groups to the number of moles of sulfonic acid ranges from 0.25 to 0.5.

20. The process as defined by claim 1, wherein the reaction is carried out in the absence of an organic solvent or in the presence of an inert organic solvent.

21. The process as defined by claim 1, wherein the reaction is carried out at normal pressure.

22. The process as defined by claim 1, wherein the reaction is carried out at a temperature ranging from 80° C. to 180° C.

23. The process as defined by claim 1, wherein the reagent is heated to a selected reaction temperature; the sulfonic acid is added progressively; and then the sulfonic anhydride formed is recovered.

24. The process as defined by claim 23, wherein a benzoyl o-trichloromethyl chloride employed in equilibrium with its pseudochloride tautomer is heated to the selected reaction temperature; trifluoromethanesulfonic acid is added progressively; and then a gaseous stream of triflic anhydride and hydrochloric acid is recovered.

25. The process as defined by claim 1, comprising the preparation of triflic anhydride.

* * * * *

UNITED STATES PATENT AND TRADEMARK OFFICE
CERTIFICATE OF CORRECTION

| | | |
|---|---|---|
| PATENT NO. | : 8,222,450 B2 | Page 1 of 1 |
| APPLICATION NO. | : 12/375073 | |
| DATED | : July 17, 2012 | |
| INVENTOR(S) | : Bernard Besson | |

It is certified that error appears in the above-identified patent and that said Letters Patent is hereby corrected as shown below:

Title Page, Section 73 (Assignee): please add --Rhodia Operations, Aubervilliers (FR)--

Signed and Sealed this
Twenty-third Day of October, 2012

David J. Kappos
*Director of the United States Patent and Trademark Office*